United States Patent [19]

Dorman et al.

[11] 4,419,453

[45] Dec. 6, 1983

[54] IMMUNOLOGICAL AGGLUTINATION ASSAYS WITH DYED OR COLORED LATEX AND KITS

[75] Inventors: Linneaus C. Dorman, Midland, Mich.; Leigh B. Bangs, Carmel, Ind.

[73] Assignee: The Dow Chemical Company, Midland, Mich.

[21] Appl. No.: 431,528

[22] Filed: Sep. 30, 1982

Related U.S. Application Data

[63] Continuation-in-part of Ser. No. 306,067, Sep. 28, 1981, abandoned.

[51] Int. Cl.³ .................... G01N 33/54; G01N 33/76
[52] U.S. Cl. .................................. 436/534; 436/510; 436/533; 436/805; 436/808; 436/814; 436/818
[58] Field of Search .............. 422/61; 436/510, 534, 436/805, 808, 814, 818

[56] References Cited

U.S. PATENT DOCUMENTS

| | | | |
|---|---|---|---|
| 3,850,752 | 11/1974 | Schuurs | 424/12 X |
| 3,882,224 | 5/1975 | Forgione | 424/8 |
| 3,920,580 | 11/1975 | Mast | 422/56 X |
| 3,949,065 | 4/1976 | Forgione | 424/8 |
| 4,016,043 | 4/1977 | Schuurs | 435/7 |
| 4,107,287 | 8/1978 | Morton | 424/12 X |
| 4,148,748 | 4/1979 | Hanlon | 252/408 |
| 4,152,411 | 5/1979 | Schall | 424/1 |
| 4,169,012 | 9/1979 | Dawson | 435/7 |
| 4,210,723 | 7/1980 | Dorman | 435/180 |
| 4,278,653 | 7/1981 | Harris | 23/230 B |
| 4,302,536 | 11/1981 | Longenecker | 435/7 |
| 4,305,721 | 12/1981 | Bernstein | 422/61 X |
| 4,373,932 | 2/1983 | Gribnav | 436/805 X |

FOREIGN PATENT DOCUMENTS

| | | |
|---|---|---|
| WO82/00060 | 1/1982 | PCT Int'l Appl. |
| 1563299 | 3/1980 | United Kingdom |

OTHER PUBLICATIONS

Polysciences, Inc., Technical information data sheet No. 238, 1980.
The Clinical Consumer Report, vol. 2(5), pp. 65–74, Mar. 1976.
Wheaton Industries Advertising Literature, Wheaton Scientific, Millville, N.J. 08332, circa Jul. 1978.
Population Reports, Series J., No. 7, pp. J–109–J–124, Nov. 1975.
J. M. Porres et al., A.J.C.P. vol. 64, 452–463 (Oct. 1975).
Sister Frances McIsaac et al., Amer. J. Obstet. Gynec., 109(8), 1213–1215 (Apr. 1971).

*Primary Examiner*—Sidney Marantz
*Attorney, Agent, or Firm*—John M. Sanders

[57] ABSTRACT

Latex agglutination test methods and kits. Employing dyed latex polymer particles and adding a water-soluble, non-latex polymer particle absorbing dye contrasting in color to the dyed latex polymer particles produces a reaction mixture that changes color when agglutination occurs. Direct and indirect latex agglutination tests are contemplated which are useful in detecting disease states or physiological states such as pregnancy.

31 Claims, No Drawings

IMMUNOLOGICAL AGGLUTINATION ASSAYS WITH DYED OR COLORED LATEX AND KITS

CROSS-REFERENCE TO RELATED APPLICATION

The present application is a continuation-in-part of our copending application Ser. No. 306,067, filed Sept. 28, 1981, abandoned.

FIELD OF THE INVENTION

This invention relates to colored latex agglutination test methods useful for detecting the presence of immunochemicals, such as antibodies and immunogens, in a biological sample and also to compositions and kits employed in such uses. Immunogens can be antigens, haptens, proteins, or polysaccharides.

BACKGROUND OF THE INVENTION

The antigen-antibody reaction is the basis for all immunological test methods. Special proteins called antibodies are produced by mammals in response to the presence of an antigen, that is a foreign substance, usually a protein. This normal body response to a foreign protein had led to the development of a number of techniques which are used to diagnose various mammalian diseases, disorders and physiological conditions, such as pregnancy, which is neither a disease nor a disorder. In vitro tests for the presence of a suspected protein, antigen or antibody in a biological sample are carried out by adding the immunological counterpart to the biological sample, i.e., add antigen if the test is for the presence of antibody or add antibody if the test is for the presence of antigen. If the suspected protein is present, and resulting antigen-antibody reaction can be demonstrated by precipitation or agglutination of the antigen-antibody complex. This antigen-antibody reaction is usually very difficult to detect visually. For this reason either antibodies or antigens are bound to latex polymer particles so that when agglutination involving the antigen or, alternatively, the antibody bound to the latex particles, does occur it can be detected visually. Agglutination is characterized by the clumping of the latex polymer particles from an otherwise smooth suspension.

In a direct latex agglutination test for the detection of the presence of an antigen in a biological sample, the biological sample is mixed with a suspension containing antibodies of said antigen bound to latex polymer particles. If antigen is present in the sample it will react with the antibodies to form an agglutant also referred to as clumps or precipitant. If no antigen is present in the sample the mixture will keep its appearance as a smooth suspension. A direct latex agglutination test for the detection of an antibody in a biological sample works on similar principles whereby antigen of said antibody are bound to latex particles.

In an indirect latex agglutination test for the detection of the presence of an antigen in a biological sample, the sample is mixed with antibodies of said antigen and allowed to incubate. If antigens are present in the biological sample they will inactivate (form a complex with) the antibodies so that when a latex-antigen suspension is subsequently added to the reaction mixture no agglutination will occur and the test mixture retains a smooth suspension appearance indicating a positive response. If no antigens are present in the biological sample then antibodies are available to react with a latex-antigen suspension when it is introduced into the reaction mixture resulting in agglutination indicating a negative result. An indirect latex agglutination test for the detection of the presence of antibodies in a biological sample works on similar principles whereby the sample is initially mixed with antigens and thereafter mixed with antibodies bound to latex particles.

Some commercial examples of agglutination tube tests for pregnancy are Pregnosticon Accuspheres ® (Organon, Inc.) and Placentex ® (Hoffman-LaRoche) which are latex tests and UCG-Lyphotest ® (Wampole Labs) which is a hemagglutination test. These tube test kits have been evaluated by *The Clinical Consumer Report*, Vol. 2, No. 5 (March 1976) and found to be generally more accurate than slide agglutination tests in which the reagents and samples are combined on a microscope slide. There are also tube tests for pregnancy sold over-the-counter for home use. These are hemagglutination tests, i.e. Predictor ® and Confidelle ® (Denver Laboratories, Canada, Ltd.).

In any of these latex agglutination tests for pregnancy, whether direct or indirect, a change in the white suspension from a smooth colloidal state to a clumped, precipitated or agglutinated state must occur as an indicator of the presence (direct test) or absence (indirect test) of human chorionic gonadotropin (HCG). This distinction in white light may be difficult, particularly for the inexperienced technician as well as the untrained observer.

In the hemagglutination tube tests for pregnancy the indirect or inhibition method is generally used. In this test non-agglutinated HCG-coated red blood cells roll down the sides of the tube and settle in a ring pattern on the bottom indicating a positive test, whereas agglutinated cells form a loose network which stays on the sloping sides of the tube indicating a negative test. Some problems with this method are that the rings are not always well defined and if the tube is jarred during the incubation period the vibration may cause the loose network to break up and cells may slide down to the bottom of the tube resulting in inconclusive results characterized by atypical rings. See *Am. J. Clin. Path.*, 64, 452 (1975) and *Population Reports* Series J, Number 7, pp. J-110–J-124 (1975) which is a publication of the Department of Medical and Public Affairs, The George Washington University Medical Center, Washington, D.C.

The present invention remedies the above mentioned problems in the prior art by making the outcome or test result of an immunological latex agglutination test much easier to discern and interpret. In this invention the observer has two indices of a test response which are (1) the appearance of a distinctly colored agglutant having formed from a smooth suspension of a contrasting color and (2) a color change in the test medium itself. Such a test will be advantageous not only to the experienced laboratory technician or physician but will also be suitable for use by the inexperienced individual in the home.

Another advantage of the present invention over hemagglutination inhibition tests is that the agglutant does not have to settle in a particular ring pattern. Thus, the test of the present invention is much less sensitive to accidental jarring or disturbances during the incubation period.

SUMMARY OF THE INVENTION

The present invention relates to an improved latex agglutination test wherein the improvement comprises employing dyed latex polymers and conducting said test in the presence of a water-soluble, non-latex polymer particle adsorbing dye which is contrasting in color to the dyed latex polymer particles. The dyed latex polymer particles and the water-soluble, non-latex polymer particle adsorbing dye, when mixed, produce an initial reaction mixture which is a suspension having a color that is a blend of the water-soluble, non-latex polymer particle adsorbing dye and the dyed latex polymer particles. If no agglutination occurs, the reaction mixture remains a suspension with no color change. If agglutination does occur, a color change in the reaction mixture is observed which is characterized by the appearance of the true color of the dyed latex polymer particles, intensified by clumping or precipitation of the dyed latex polymer particles, and the appearance of the remainder of the reaction mixture being that of the water-soluble, non-latex polymer particle adsorbing dye.

DETAILED DESCRIPTION OF THE EMBODIMENTS

In the practice of this invention where the presence of an immunochemical is to be determined, it is essential to employ:

(a) a biological sample;

(b) an immunological counterpart to said immunochemical;

(c) dyed latex polymer particles having said immunochemical bound thereto; and (d) a water-soluble, non-latex polymer particle adsorbing dye contrasting in color to the dyed latex polymer particles.

When used herein the term "immunochemical" is meant to encompass antibodies and immunogens. The term "immunogen" is meant to encompass antigens, including non-proteinaceous antigens, proteins, haptens and polysaccharides.

Biological samples to be tested for the presence of an immunochemical are obtained from mammals such as humans. A biological sample is any body sample or body fluid which would contain an immunochemical, the presence of which is to be determined. Examples of biological samples are urine, saliva, synovial fluid, cerebrospinal fluid, sputum, whole blood, serum, plasma or any other fractionable portion of whole blood. When pregnancy is to be determined by the process of this invention it is preferred to use a female's urine as the biological sample.

The immunological counterpart to said immunochemical is required in order to react with immunochemical present in the biological sample or, if there is no immunochemical in the sample, to react with the immunochemical bound to the dyed latex polymer particles. Immunological counterparts of an immunochemical are any substances that react with a specific immunochemical resulting in precipitation or agglutination. For example, antibodies of a specific antigen are the immunological counterpart to that specific antigen and conversely, an antigen is an immunological counterpart for antibodies that react with that antigen. Antibodies are usually proteins. The usual method of obtaining antibodies is to innoculate an antigen into an animal that will respond immunologically to form an antibody to that specific antigen and then extract the serum containing said antibodies. For example, in the case of antibodies to HCG for use in pregnancy tests, rabbit anti-HCG serum is preferred and is commercially available. The amount of antiserum to be used varies depending on the antigen to be detected and is readily determinable by one skilled in the art.

Antigens or antibodies bound to dyed latex polymer particles, such as, for example, blue, red, green, orange, yellow, or plain white latex polymer particles, are required to detect agglutination. The term "dyed latex polymer particles" encompasses dyed white latex polymer particles as well as plain white latex polymer particles. It is well known in the art that latex polymer particles can be dyed. It is also known in the art that protein substances (antigens, haptens and antibodies) can be coupled to latex polymer particles. In the practice of the present invention it is preferred to couple antigens, haptens or antibodies to epoxylated latex in substantial accordance with U.S. Pat. No. 4,210,723 which is hereby incorporated herein by reference and made a part hereof. A preferred latex is styrene-glycidyl methacrylate (SGM) latex colored with a dye. Materials substantially equivalent to styrene-glycidyl methacrylate listed in U.S. Pat. No. 4,210,723 are acceptable latex polymer particles that can also be used in the practice of this invention. Also acceptable are styrene-based latexes and derivatives thereof, such as, for example, latexes with functional surface groups such as carboxylic (styrene/acrylic acid, styrene/butadiene acrylic acid) and amide (styrene/acrylamide) functional groups.

A water-soluble, non-latex polymer particle adsorbing dye, when added to the reaction medium, gives the reaction medium an initial color which is a blend of the dyed latex polymer particles and the water-soluble, non-latex polymer particle adsorbing dye. When agglutination occurs between the immunochemical and its immunological counterpart bound to the dyed latex polymer particles the agglutant (such as antibody/antigen-latex complex) settles out of the reaction mixture. The agglutant thus formed is the color of the dyed latex polymer particles while the rest of the test medium takes on the color of an aqueous solution of said water-soluble, non-latex polymer particle adsorbing dye at the pH and concentration existing in the reaction medium. When no agglutination occurs between the immunological counterpart bound to the dyed latex polymers and immunochemical then the reaction mixture retains a smooth suspension appearance which has a color which is a blend of the dyed latex polymer particles and the water-soluble, non-latex polymer particle adsorbing dye. The water-soluble, non-latex polymer particle adsorbing dye can be any dye which does not adversely affect the color of the dyed latex polymer particles, i.e. it is not adsorbed by the latex polymer particles. Suitable water-soluble, non-latex polymer particle adsorbing dyes are Amocid yellow (American Aniline Products) and brilliant crocein 3BA red dye. While the exact concentration of water-soluble non-latex polymer particle adsorbing dye is not critical, enough dye must be present to impart a color in the reaction medium. It is preferred that the water soluble non-latex, polymer particle adsorbing dye be present in the test medium in the range of from about 0.03 to about 3 percent by weight of latex polymer solids and even more preferably about 0.3 percent by weight of latex polymer solids.

In the practice of this invention the water-soluble, non-latex polymer particle adsorbing dye must be a different or contrasting color than the dyed latex polymer particles so a contrasting color scheme appears when agglutination occurs. Different or contrasting colors are meant to encompass any visually distinguishable colors. For example, when the latex polymer particles are dyed blue and the water-soluble, non-latex polymer particle adsorbing dye is red, a purple suspension is formed when the two are mixed. When agglutination occurs the agglutant is blue and the rest of the reaction medium is red. Thus, a three color scheme is observed when agglutination occurs (purple to red and blue).

The present invention may be carried out in any acceptable vessel, such as, for example a clear test tube. It may also be carried out as a slide test by mixing the reagents on a slide such as a microscope slide and observing if agglutination takes place. Open ended capillary tubes with an inside diameter of from about 1 to about 5 millimeters (mm) may also be used providing the reagents are premixed as described herein and drawn up after the last mixing step by capillary action. It is preferred to employ vials having a cone shaped bottom which intensifies the color of the agglutant. Commercial tubes such as, 0.1 ml conical boro-silicate micro product V vials (Catalog No. 986211) are examples of cone shaped vials manufactured by Wheaton Scientific, Millville, N.J. 08322.

The present colored agglutination tests are advantageously carried out at a temperature in the range of from about 20° C. to about 37° C. Below this range the immunological reaction is slowed down making the test time longer and above this range adverse reactions may occur which could indicate false results.

While it is not critical what volume of reagents are mixed together, it is preferred that equal volumes of biological sample, antibody and antigen bound to dyed latex particles are mixed together. In order to be more economical, it is preferred that portions in the range of from about 25 to about 100 microliters ($\mu$l) of the above mentioned reagents be mixed as herein described. When mixing any of the ingredients described herein it is preferred to gently stir them with a glass rod or gently shake the reaction vessel which contains said ingredients.

In conducting an indirect latex agglutination test for detecting the presence or absence of an immunochemical according to the present invention, a biological sample is admixed with the immunological counterpart of said immunochemical and allowed to incubate for at least about 1 minute. This incubation period allows any immunochemical present in the biological sample to react with its immunological counterpart. Below 1 minute any be insufficient time for this reaction to occur, thus, leading to false results. An incubation period longer than about 15 minutes is not necessary but would not be detrimental. A preferred incubation time is 5 minutes. After the incubation period, dyed latex polymer particles, having immunochemical bound therto, are then added to the reaction medium and allowed to react for at least about 30 minutes and preferably about 120 minutes. At the point where the immunochemical bound to dyed latex polymer particles is added to the reaction, or at any time before, or after, a water-soluble, non-latex polymer adsorbing dye which is contrasting in color to the dyed latex polymer particles is added to the reaction mixture. The 30 minute reaction period allows any available immunological counterpart of said immunochemical to react with the immunochemical bound to the dyed latex polymer particles which would form an agglutant and settle out of the reaction mixture. This indicates a negative test result. If immunochemical is present in the biological sample, then there would be no immunological counterpart available to react with the immunochemical bound to the dyed latex polymer particles which would result in the reaction medium appearing as a smooth suspension. This indicates a positive test result (immunochemical is present in the biological sample).

A preferred embodiment of the present invention is a method for detecting the presence of HCG in a female's urine which, if positive, would indicate that the female is pregnant. In conducting such a test about 25 $\mu$l of urine are mixed in a reaction tube with about 25 $\mu$l of glycine buffer containing 10% (v/v) of a 0.1% solution of brilliant crocein 3BA red dye, 25 $\mu$l of HCG-antiserum (titer 1:1280 in phosphate buffer) and allowed to incubate for about 5 minutes. Then 25 $\mu$l of glycine buffer, containing about 3.5% polymer solids of blue-dyed styrene-glycidyl methacrylate (SGM) latex with HCG bound covalently to it, is added. This reaction mixture, which appears as a homogeneous purple suspension, is then mixed and allowed to stand for about 2 hours. If the reaction mixture retains the appearance of a purple suspension after 2 hours then the test is positive (HCG is present in the urine and the female is pregnant). If the reaction medium shows a distinct blue mass of polymer agglutant in the bottom of the tube and a tendency toward restoration of the red color of the crocein dye in the rest of the reaction mixture then the test is negative (HCG not present in the urine and the female is not pregnant). This type of latex agglutination test is referred to as an indirect latex agglutination test. The glycine buffer referred to in this preferred embodiment is prepared substantially in accordance with the teachings in E. J. Mellinger, *Thrombos Diather. Haemorrh.*, 23, 211 (1970) which is incorporated herein by reference. The phosphate buffer referred to is prepared by diluting with water 3.68 ml of 0.5 M $KH_2PO_4$, 32.2 ml of $Na_2HPO_4$, 5.84 g of NaCl and 10 ml of 1% Merthiolate ® to one liter. This gives a phosphate buffer with a pH of 8.0 at 5° C. The buffers employed in this preferred embodiment keep the pH of the reaction mixture at from about 6 to about 9 which is advantageous for the immunological reaction between antigens and antibodies.

In another aspect of the present invention an indirect colored latex agglutination test kit is used in testing biological samples for the presence of an immunochemical, i.e., protein, polysaccharide, antigen, hapten of antibody, said kit comprising:

(a) a first reagent containing dyed latex polymer particles having said immunochemical bound thereto;

(b) a second reagent containing an immunological counterpart for said immunochemical; and (c) a third reagent containing a water-soluble, non-latex polymer particle adsorbing dye which is contrasting in color to the dyed latex polymer particles.

The kit may also be a 2 reagent kit whereby the water-soluble, non-latex polymer particle adsorbing dye is premixed with either the first or second reagent. The above reagents are prepared and used as herein described. In a preferred embodiment, the first reagent is HCG covalently bound to dyed SGM latex polymer particles, the second reagent is rabbit anti-HCG serum and the third reagent is a water-soluble, non-latex polymer particle adsorbing dye which is contrasting in color to the dyed latex polymer particles.

Alternatively, a direct latex agglutination test may be carried out according to the present invention by binding an immunological counterpart of an immunochemical to dyed latex polymer particles and then admixing a biological sample with the immunological counterpart-dyed latex material in the presence of a water-soluble, non-latex polymer particle adsorbing dye which is contrasting in color to the dyed latex polymer particles. In this test a positive result (immunochemical present in sample) is characterized by an agglutant settling out of the reaction mixture. The agglutant thus formed is the color of the dyed latex polymer particles while the rest of the reaction medium takes on the color of the water-soluble, non-latex polymer particle adsorbing dye. A negative (no immunochemical present in sample) result is characterized by the reaction medium appearing as a homogenous latex suspension having a color which is a blend of the dyed latex polymer particle and the water-soluble, non-latex polymer particle adsorbing dye.

In conducting a direct colored latex agglutination test, conveniently, equal volumes of a biological sample, immunological counterpart-dyed latex, and water-soluble, non-latex polymer particle adsorbing dye which is contrasting in color to the dyed latex are combined in an appropriate vessel and this mixture is allowed to incubate for at least about 30 minutes and preferably about 2 hours. The results of the test for the detection of the presence of antigen in the biological sample are determined by the presence or absence of agglutination as described above.

A typical direct latex agglutination test kit, according to the present invention, useful for testing biological samples for the presence of an immunochemical, i.e., protein, antigen, hapten or antibody, comprises a reagent comprising dyed latex polymer particles having an immunological counterpart of said immunochemical bound thereto and a water-soluble, non-latex polymer particle adsorbing dye that is contrasting in color to said dyed latex polymer particles. The kit may also be a 2 reagent kit whereby the water-soluble, non-latex polymer particle adsorbing dye is employed as a separate reagent and added to the reaction mixture.

When testing for pregnancy, it is preferred to use the indirect latex agglutination test because of the prozone phenomenon seen in the direct agglutination test for pregnancy (see *Amer. J. Obstet. Gynec.*, Vol. 109, No. 8, pp. 1213-1215, Apr. 15, 1971).

The following examples illustrate the present invention and the manner by which it can be practiced but, as such, are not to be construed as limitations upon the overall scope of the same.

EXAMPLE I

Preparation of Dyed Latex Particles

To 100 grams (g) (14.2 g polymer solids) of styrene-glycidyl methacrylate (SGM) latex 0.67 micrometer ($\mu$m) diameter) and 200 g of deionized water, was added 15 g of benzene which contained 0.015 g of Calco Oil Blue N dye (C.I. #61552). The dye solution was added to the latex over a 30 minute time period while mixing the latex with a half moon blade stirrer turning at about 250 revolutions per minute (rpm). After 24 hours the dyed latex was placed in a one liter flask and the benzene was removed in vacuo by using a Rinco ® evaporator at a temperature of about 35° C. The resulting latex polymer solids were blue in color, had a polymer solid content of 6.3% and a surface epoxy content of about 0.17 mequiv/g polymer solids.

EXAMPLE II

Binding HCG to Dyed Latex

A 5.84 g (0.37 g polymer) portion of the dyed latex prepared in Example 1 and a solution of 4,000 I.U. of HCG (lot 75C-00331) in 2 ml of phosphate buffer was stirred gently at about 5° C. for 4.5 days. This reaction mixture was worked up by centrifugation (2×) and finally reconstituted in glycine buffer to 10 g (about 3.5% polymer solids) of blue-dyed styrene-glycidyl methacrylate latex-HCG, hereinafter referred to as Preparation No. 1.

EXAMPLE III

Binding HCG to Dyed Latex

A procedure in substantial accordance with Example II was carried out using 7.30 g (0.46 g polymer solids) of dyed-latex and a solution of 10,000 I.U. of HCG (lot 75C-0021) in 3 ml of phosphate buffer. There was obtained 15.1 g (2.9% polymer solids) of blue-dyed styrene-glycidyl methacrylate latex-HCG, hereinafter referred to as Preparation No. 2.

EXAMPLE IV

Agglutant Compared to Non-agglutant Visual Results

The following ingredients were added to 2 reaction tubes (capillary tubes with an inside diameter of about 2 to 3 mm with a sealed lower tip):

| Tube 1 | | Tube 2 | |
|---|---|---|---|
| (i) | 50 $\mu$l glycine buffer containing 10% (v/v) 0.1% solution crocein 3BA red dye | (i) | (Same as 1) |
| (ii) | 25 $\mu$l Preparation No. 1 | (ii) | (Same as 1) |
| (iii) | 25 $\mu$l HCG antiserum (titer 1:1280 in phosphate buffer) | (iii) | 25 $\mu$l phosphate buffer |

The contents of the tubes were mixed. The contents of both tubes acquired a homogeneous purple coloration after mixing. Within 2 hours, the mixture in Tube 1 showed a distinct blue mass of polymer agglutant in the capillary tip of the reaction tube and a tendency toward restoration of the red color of the crocein dye in the buffer. Tube 2, containing no antiserum was still completely homogenously purple colored after 2 hours. After 6 hours, Tube 2 was still homogeneously purple colored while in Tube 1 the agglutination of the latex polymer with the antiserum was essentially complete and the color of the contents of Tube 1 was red with a blue color of agglutant mass at the bottom of the capillary tube.

EXAMPLE V

Indirect Latex Agglutination Test

Latex agglutination inhibition tube tests were conducted using tubes and reagents described in Example IV plus solutions of HCG in phosphate buffer at concentrations of 1.25, 2.5 and 5.0 I.U. of HCG per milliliter (I.U. HCG/ml). The quantity in microliters ($\mu$l) and order of mixing is outlined as follows:

| Reagent Added | Tube No. | | | | |
|---|---|---|---|---|---|
| | 1 | 2 | 3 | 4 | 5 |
| 1. glycine buffer-crocein dye solution | 75 μl | 25 μl | 25 μl | 25 μl | 50 μl |
| 2. 1.25 I.U. HCG/ml | —* | 25 μl | — | — | — |
| 3. 2.5 I.U. HCG/ml | — | — | 25 μl | — | — |
| 4. 5.0 I.U. HCG/ml | — | — | — | 25 μl | — |
| 5. HCG antiserum solution | — | 25 μl | 25 μl | 25 μl | 25 μl |
| 6. Latex HCG (Preparation No. 1) | 25 μl | 25 μl | 25 μl | 25 μl | 25 μl |

*"—" denotes absence of reagent in corresponding tube.

The tubes' contents with Reagents 1-5 were mixed and let stand for 15 minutes before the 25 μl of latex-HCG (Preparation No. 1) was added to each tube. The tubes contents were again mixed and the tubes were suspended vertically against a white background. After 95 minutes, characteristic blue tips of agglutant were observed in tubes 2 and 5 whereas tubes 1 and 4 were homogeneously purple. Tube 3 had a small amount of blue tip agglutant. Therefore, the detection sensitivity for HCG in this test was >2.5 <5 I.U. HCG/ml.

EXAMPLE VI

Indirect Latex Agglutination Test

Latex agglutination inhibition tube tests were conducted substantially in accordance with Example V except the reagents and order of mixing them were different as indicated.

| Reagent Added | Tube No. | | | |
|---|---|---|---|---|
| | 1 | 2 | 3 | 4 |
| 1. glycine buffer | 100 μl | — | — | 50 μl |
| 2. 2 I.U. HCG/ml$^A$ | —* | 50 μl | — | — |
| 3. 4 I.U. HCG/ml$^A$ | — | — | 50 μl | — |
| 4. HCG Antiserum Solution$^A$ | — | 50 μl | 50 μl | 50 μl |
| 5. 0.1% crocein red dye solution | 5 μl | 5 μl | 5 μl | 5 μl |
| 6. Latex-HCG (Preparation No. 2) | 50 μl | 50 μl | 50 μl | 50 μl |

*"—" denotes absence of reagent in corresponding tube.
$^A$denotes glycine buffer The tubes' contents with Reagents 1-4 were mixed and let stand for 15 minutes before 5 μl of 0.1% crocein red dye solution and 50 μl of latex-HCG (Preparation No. 2) were added to each of the tubes. After the addition of Reagents 5 and 6, the tubes were mixed and allowed to stand for 2 hours. After 2 hours, a characteristic blue tip agglutant had formed in tube 4 whereas tubes 1-3 were homogeneously purple indicating that the sensitivity for detecting HCG in this test was ≧2 I.U. HCG/ml.

EXAMPLE VII

Indirect Latex Agglutination Test

Latex agglutination inhibition tube tests were conducted substantially in accordance with Example VI except that the crocein red dye solution (0.1%) was premixed with latex-HCG (Preparation No. 2) to give a purple colored latex suspension. The detection sensitivity for HCG was unchanged from that in Example VI (≧2 I.U. HCG/ml). This purple crocein dye/latex-HCG suspension was stable and there was no tendency for the latex particles to absorb or adsorb the water-soluble crocein red dye upon standing in a refrigerator at about from 2° to about 8° C., which is the customary storage conditions for latex-HCG reagents. Blue latex-HCG particles slowly settled out on standing revealing the red color of the water soluble dye but the particles were readily resuspended by shaking, thereby restoring the purple color of the suspension.

The practice of this invention enables one to immunologically determine the presence or absence of disease states, such as, for example, syphilis, tuberculosis, hydatidiform mole, measles, choriocarcinoma, rheumatoid arthritis and hepatitis and physiological conditions such as, for example, pregnancy. It is readily apparent that the practice of the present invention pertains to any latex agglutination test, either direct or indirect, whereby agglutination is characterized by a color change in reaction mixture as described herein.

What is claimed is:

1. In a method for detecting the presence of an immunochemical in a biological sample using an indirect latex agglutination test which comprises
   (i) admixing an immunological counterpart of said immunochemical with said biological sample to form a reaction mixture;
   (ii) allowing said reaction mixture to incubate for at least about one minute;
   (iii) adding latex polymer particles, having said immunochemical bound thereto, to said reaction mixture; and then
   (iv) determining if agglutination occurs by the aggregation of polymer particles;
the improvement which comprises:
   (a) employing dyed latex polymer particles having said immunochemical bound thereto;
   (b) carrying out said method in the presence of a water-soluble, non-latex polymer particle adsorbing dye that is contrasting in color to the dyed latex polymer particles; and
   (c) determining if agglutination occurs by observing a color change in the reaction mixture which is characterized by the appearance of the true color of the dyed latex polymer particles, intensified by clumping or precipitation of the dyed latex polymer particles, and the appearance of the remainder of reaction mixture being that of the water-soluble, non-latex polymer particle adsorbing dye.

2. The method of claim 1 wherein said immunochemical is an antigen and said immunological counterpart is an antibody of said antigen.

3. The method of claim 2 wherein said antigen is human chorionic gonadotropin (HCG) and said antibody is HCG-antiserum.

4. The method of claim 3 wherein said biological sample is a female human's urine.

5. The method of claim 1 wherein said water-soluble, non-latex polymer particle adsorbing dye is introduced into said reaction mixture during step (i), (ii) or (iii).

6. The method of claim 1 wherein said biological sample, biological counterpart of said immunochemical, immunochemical bound to dyed latex polymer particles and water-soluble, non-latex polymer particle adsorbing dye are admixed in about equal volumetric amounts.

7. The method of claim 1 wherein said dyed latex polymer particles are dyed or plain white styrene-glycidyl methacrylate latex polymer particles.

8. The method of claim 1 wherein said immunological counterpart of said immunochemical is an antigen and said immunochemical is an antibody of said antigen.

9. The method of claim 1 wherein said immunochemical is a protein, an antibody, an antigen, a hapten or a polysaccharide.

10. In a method for detecting the presence of an immunochemical in a biological sample using a direct latex agglutination test which comprises
(i) admixing said biological sample with latex polymer particles having an immunological counterpart of said immunochemical bound thereto, to form a reaction mixture;
(ii) allowing said reaction mixture to incubate for at least about 30 minutes; and then
(iii) determining if agglutination occurs;
the improvement which comprises:
(a) employing dyed latex polymer particles having said immunological counterpart of said immunochemical bound thereto;
(b) carrying out said method in the presence of a water-soluble, non-latex polymer particle adsorbing dye that is contrasting in color to the dyed latex polymer particles; and
(c) determining if agglutination occurs by observing a color change in the reaction mixture which is characterized by the appearance of the true color of the dyed latex polymer particles, intensified by clumping or precipitation of the dyed latex polymer particles, and the appearance of the remainder of reaction mixture being that of the water-soluble, non-latex polymer particle adsorbing dye.

11. The method of claim 10 wherein said immunochemical is an antigen and said immunological counterpart is an antibody of said antigen.

12. The method of claim 11 wherein said antigen is human chorionic gonadotropin (HCG) and said antibody is HCG-antiserum.

13. The method of claim 12 wherein said biological sample is a female human's urine.

14. The method of claim 10 wherein said water-soluble, non-latex polymer particle adsorbing dye is introduced into said reaction mixture at any time prior to the incubation period.

15. The method of claim 10 wherein said dyed latex polymer particles are dyed or plain white styrene-glycidyl methacrylate latex polymer particles.

16. The method of claim 10 wherein said immunological counterpart of said immunochemical is an antigen and said immunochemical is an antibody of said antigen.

17. The method of claim 10 wherein said immunochemical is a protein, an antibody, an antigen, a hapten or a polysaccharide.

18. An indirect latex agglutination test kit for detecting the presence of an immunochemical in a biological sample comprising:

(i) a first reagent comprising an immunological counterpart of said immunochemical;
(ii) a second reagent comprising dyed latex polymer particles hving said immunochemical bound thereto; and
(iii) a third reagent, comprising a water-soluble, non-latex polymer particle adsorbing dye that is contrasting in color to said dyed latex polymer particles.

19. The kit of claim 18 wherein said immunochemical is an antigen and said immunological counterpart is an antibody of said antigen.

20. The kit of claim 19 wherein said antigen is human chorionic gonadotropin (HCG) and said antibody is HCG-antiserum.

21. The kit of claim 20 wherein said dyed latex polymer particles are dyed or plain white styrene-glycidyl methacrylate latex polymer particles.

22. The kit of claim 18 wherein said immunological counterpart of said immunochemical is an antigen and said immunochemical is an antibody of said antigen.

23. The kit of claim 18 wherein said third reagent is premixed with either the first or second reagent.

24. The kit of claim 18 wherein said immunochemical is a protein, an antibody, an antigen, a hapten or a polysaccharide.

25. A direct latex agglutination test kit for detecting the presence of an immunochemical in a biological sample comprising a reagent containing dyed latex polymer particles having an immunological counterpart of said immunochemical bound thereto, and a water-soluble, non-latex polymer particle adsorbing dye that is contrasting in color to said dyed latex polymer particles.

26. The kit of claim 25 wherein said immunochemical is an antigen and said immunological counterpart is an antibody of said antigen.

27. The kit of claim 26 wherein said antigen is human chorionic gonadotropin (HCG) and said antibody is HCG antiserum.

28. The kit of claim 27 wherein said dyed latex polymer particles are dyed or plain white styrene-glycidyl methacrylate latex polymer particles.

29. The kit of claim 25 wherein said immunological counterpart of said immunochemical is an antigen and said immunochemical is an antibody of said antigen.

30. The kit of claim 25 wherein said water-soluble non-latex polymer particle adsorbing dye is present as a second reagent.

31. The kit of claim 25 wherein said immunochemical is a protein, an antibody, an antigen, a hapten or a polysaccharide.

* * * * *

UNITED STATES PATENT AND TRADEMARK OFFICE
CERTIFICATE OF CORRECTION

PATENT NO. : 4,419,453
DATED : December 6, 1983
INVENTOR(S) : Linneaus C. Dorman; Leigh B. Bangs It is certified that error appears in the above—identified patent and that said Letters Patent is hereby corrected as shown below:

Title page, second column, under "Abstract", third line down, "absorbing" should read --adsorbing--.

Column 1, line 25, "had" should read --has--.

Column 1, line 35, "and" should read --the--.

Column 5, line 25, "08322" should read --08332--.

Column 5, line 50, "any" should read --may--.

Column 5, line 56, "therto" should read --thereto--.

Column 6, line 50, "of" should read --or--.

Column 12, line 4, "hving" should read --having--.

Signed and Sealed this

Eighth Day of May 1984

[SEAL]

Attest:

GERALD J. MOSSINGHOFF

Attesting Officer

Commissioner of Patents and Trademarks